United States Patent [19]

Lesher et al.

[11] Patent Number: 4,634,772

[45] Date of Patent: Jan. 6, 1987

[54] 2-[2-(DI-LOWER-ALKYLAMINO)-1-PROPENYL]-6-METHOXY-3-PYRIDINECARBONITRILES, INTERMEDIATES FOR CARDIOTONIC AGENTS

[75] Inventors: George Y. Lesher, Schodack; Baldev Singh, East Greenbush, both of N.Y.

[73] Assignee: Sterling Drug Inc., New York, N.Y.

[21] Appl. No.: 816,591

[22] Filed: Jan. 6, 1986

Related U.S. Application Data

[63] Continuation-in-part of Ser. No. 811,040, Dec. 19, 1985, abandoned, which is a continuation-in-part of Ser. No. 765,900, Aug. 14, 1985, abandoned, which is a continuation-in-part of Ser. No. 695,603, Jan. 28, 1985, abandoned.

[51] Int. Cl.$^4$ ........................................... C07D 213/64
[52] U.S. Cl. ................................................. 546/288
[58] Field of Search ....................................... 546/288

[56] References Cited

U.S. PATENT DOCUMENTS 3,993,656  11/1976  Rooney et al. ............... 546/288
4,415,580  11/1983  Lesher et al. ................ 546/288

FOREIGN PATENT DOCUMENTS 2413864  10/1975  Fed. Rep. of Germany ...... 546/288

OTHER PUBLICATIONS

Czuba et al., Pol J. Chem. 52, 2369–76 (1978).
Paudler et al., J. Heterocyclic Chem. 2(4), 393–8 (1965).

*Primary Examiner*—Henry R. Jiles
*Assistant Examiner*—J. Richter
*Attorney, Agent, or Firm*—Thomas L. Johnson; B. Woodrow Wyatt; Paul E. Dupont

[57] ABSTRACT

2-[2-(di-lower-alkylamino-1-propenyl]-6-methoxy-3-pyridinecarbonitriles, useful as intermediates for cardiotonic agents.

2 Claims, No Drawings

2-[2-(DI-LOWER-ALKYLAMINO)-1-PROPENYL]-6-METHOXY-3-PYRIDINECARBONITRILES, INTERMEDIATES FOR CARDIOTONIC AGENTS

CROSS-REFERENCE TO RELATED APPLICATIONS

This application is a continuation-in-part of copending application Ser. No. 811,040, filed Dec. 19, 1985, now abandoned, in turn, a continuation-in-part of copending application Ser. No. 765,900, filed Aug. 14, 1985, now abandoned, in turn, a continuation-in-part of its copending application Ser. No. 695,603, filed Jan. 28, 1985 and now abandoned.

BACKGROUND OF THE INVENTION a. Field of the Invention

This invention relates to 5-[1H-(5-membered-N-aromatic-heteryl-1-yl)]-1,6-naphthyridin-2(1H)-ones, their cardiotonic use, their preparation and intermediates.

b. Information Disclosure Statement

Lesher and Singh in U.S. Pat. No. 4,415,580, issued Nov. 15, 1983, show as cardiotonic agents 5-(loweralkyl)-1,6-naphthyridin-2(1H)-ones (I) and their preparation by reacting a 5-(lower-alkanoyl)-6-methyl-2(1H)-pyridinone with di-(lower-alkyl)formamide di-(lower-alkyl) acetal to produce 5-(lower-alkanoyl)-6-[2-(di-lower-alkylamino)ethenyl]-2(1H)-pyridinone (II) and reacting II with formamidine or ammonia or salt thereof to produce I.

Czuba et al., Pol. J. Chem. 52, 2369–76 (1978), show as intermediates 4-bromo-1,6-naphthyridin-2(1H)-one and 4-hydrazino-1,6-naphthyridin-2(1H)-one. This reference also shows the preparation of 4-bromo-1,6-naphthyridin-2(1H)-one by heating 2,4-dibromo-1,6-naphthyridine with 20% hydrobromic acid and the preparation of 4-hydrazino-1,6-naphthyridin-2(1H)-one by heating 4-bromo-1,6-naphthyridin-2(1H)-one with hydrazine.

Paudler et al., J. Heterocyclic Chem. 2 (4), 393–8 (1965), show the synthesis and NMR spectra of various 4-substituted-1,6-naphthyridines, for example, the reaction of 4-hydroxy-1,6-naphthyridine with POBr$_3$ or POCl$_3$ to obtain 4-bromo-1,6-naphthyridine or 4-chloro-1,6-naphthyridine, respectively. Also shown is the reaction of 4-bromo-1,6-naphthyridine with dimethylamine to produce 4-dimethylamino-1,6-naphthyridine and the reaction 4-chloro-1,6-naphthyridine with piperidine or hydrazine to produce 4-(1-piperidinyl)-1,6-naphthyridine or 4-hydrazino-1,6-naphthyridine, respectively.

Rooney et al. U.S. Pat. No. 3,993,656, issued Nov. 23, 1976, shows various substituted-1,8-naphthyridin-2(1H)-ones having bronchodilating and hypotensive properties, including 6-(2-imidazolyl)-1,8-naphthyridin-2(1H)-one and its preparation from 2-amino-6-(2-imidazolyl)-1,8-naphthyridine.

SUMMARY OF THE INVENTION

In a composition of matter aspect the invention resides in 5-[1H-(5-membered-N-aromatic-heteryl)-1-yl]-7-R'-1,6-naphthyridin-2(1H)-one having the formula I

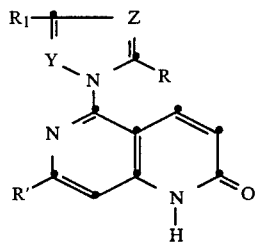

or acid-addition or cationic salt thereof, where R is hydrogen, halo or lower-alkyl, R' is hydrogen or methyl, R$_1$ is hydrogen, lower-alkyl, hydroxymethyl, halo, trifluoromethyl, nitro or phenyl, Z is N, C—H, C-(lower-alkyl), C-halo, C-hydroxymethyl or C-phenyl, and Y is N, C—H, C-halo, C-(lower-alkyl) or C—NO$_2$, at least one of Y or Z being N. The compounds of formula I are useful as cardiotonic agents, as determined by standard pharmacological evaluation procedures.

A composition aspect of the invention resides in the cardiotonic composition for increasing cardiac contractility which comprises a pharmaceutically acceptable carrier and, as the active component thereof, a cardiotonically effective amount of 5-[1H-(5-membered-N-heteryl)-1-yl]-7-R'-1,6-naphthyridin-2(1H)-one having the formula I or pharmaceutically acceptable acid-addition or cationic salt thereof.

A method aspect of the invention resides in the method for increasing cardiac contractility in a patient requiring such treatment which comprises administering orally or parenterally in a solid or liquid dosage form to such patient a cardiotonically effective amount of 5-[1H-(5-membered-N-heteryl)-1-yl]-7-R'-1,6-naphthyridin2(1H)-one having the formula I or pharmaceutically acceptable acid-addition or cationic salt thereof.

In another composition of matter aspect, the invention resides in 5-X-7-R'-1,6-naphthyridin-2(1H)-one having the formula II

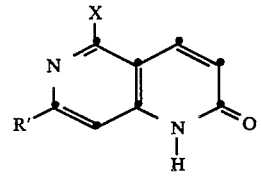

or pharmaceutically acceptable acid-addition or cationic salt thereof, where X is bromo, chloro or hydrazino and R' is methyl. The compounds of formula II where X is bromo or chloro, are useful as cardiotonic agents, as determined by standard pharmacological procedures, and also are useful as intermediates for preparing the compounds of formula I hereinabove, the compound where X is bromo being preferred when used as an intermediate. The compound of formula II where X is hydrazino is useful as an intermediate for preparing the compounds of formula I where Y is N, Z is C—H and R' is methyl.

Another composition aspect of the invention resides in the cardiotonic composition for increasing cardiac contractility which comprises a pharmaceutically acceptable carrier and, as the active component thereof, a cardiotonically effective amount of 5-X-7-R'-1,6-naphthyridin-2(1H)-one having the formula II or pharmaceutically acceptable acid-addition or cationic salt thereof, where X is bromo or chloro and R' is methyl.

A method aspect of the invention resides in the method for increasing cardiac contractility in a patient requiring such treatment which comprises administering orally or parenterally in a solid or liquid dosage form to such patient a cardiotonically effective amount of 5-X-7-R'-1,6-naphthyridin-2(1H)-one having the formula II or pharmaceutically acceptable acid-addition or cationic salt thereof, where X is bromo or chloro and R' is methyl.

In another composition of matter aspect, the invention resides in 2-[2-(di-lower-alkylamino)-1-propenyl]-6-methoxy-3-pyridinecarbonitrile having the formula IIIa

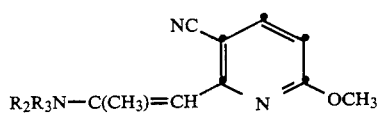

and acid-addition salt thereof, where $R_2$ and $R_2$ are each lower-alkyl.

In a process aspect the invention resides in the process which comprises reacting hydrogen bromide or hydrogen chloride with 2-[2-(di-lower-alkylamino)-1-propenyl]-6-methoxy-3-pyridinecarbonitrile to produce 5-(bromo or chloro)-2-methoxy-7-methyl-1,6-naphthyridine and treating said 2-methoxy compound with aqueous sodium or potassium hydroxide solution to produce 5-(bromo or chloro)-7-methyl-1,6-naphthyridin-2(1H)-one.

DETAILED DESCRIPTION INCLUSIVE OF PREFERRED EMBODIMENTS

Intermediates for the compounds of formula I are the 5-X-7-R'-1,6-naphthyridin-2(1H)-ones having the formula II

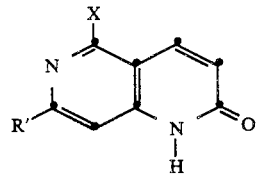

where X is bromo, chloro or hydrazino and R' is hydrogen or methyl. A preferred compound of formula II as an intermediate is the compound where X is bromo and R' is hydrogen or methyl. The compound of formula II where X is hydrazino is useful as an intermediate for preparing the compounds of formula I where Y is N and Z is C—H.

Intermediates for the compounds of formula II where X is bromo or chloro and R' is hydrogen are the 1,6-dihydro-2-[2-(di-lower-alkylamino)ethenyl]-6-oxo-3-pyridinecarbonitriles having the formula III

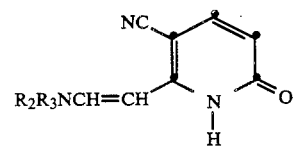

and acid-addition salts thereof, where $R_2$ and $R_3$ are each lower-alkyl.

The reaction of hydrogen bromide or hydrogen chloride with 1,6-dihydro-2-[2-(di-lower-alkylamino)-ethenyl]-6-oxo-3-pyridinecarbonitrile of formula III produces 5-bromo(or chloro)-7-R'-1,6-naphthyridin-2(1H)-one of formula II above where X is bromo or chloro and R' is hydrogen.

The intermediate for the preparation of the compounds of formula II where X is bromo or chloro and R' is methyl is 2-[2-(di-lower-alkylamino)-1-propenyl]-6-methoxy-3-pyridinecarbonitrile of the formula IIIa

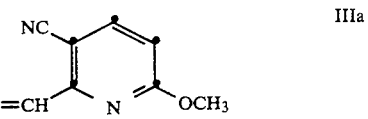

or acid-addition salt thereof, and $R_2$ and $R_3$ are each lower-alkyl.

The reaction of 6-methoxy-2-methyl-3-pyridinecarbonitrile with N,N-(di-lower-alkyl)acetamide dimethyl acetal produces 2-[2-(di-lower-alkylamino)-1-propenyl]-6-methoxy-3-pyridinecarbonitrile of formula IIIa and the reaction of the compound of formula IIIa with hydrogen bromide or hydrogen chloride followed by alkaline hydrolysis of the resulting 5-(bromo or chloro)-2-methoxy-7-methyl-1,6-naphthyridine produces 5-(bromo or chloro)-7-methyl-1,6-naphthyridin-2(1H)-one of formula II where R' is methyl The reaction of 5-bromo(or chloro)-7-R'-1,6-naphthyridin-2(1H)-one with 1H-(5-membered-N-aromatic)-heteryl compound having the formula IV

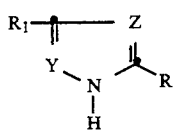

where Y, Z, R', $R_1$ and R are defined as in formula I, produces the 5-[1H-(5-membered-N-aromatic-heteryl)-1-yl]-7-R'-1,6-naphthyridin-2(1H)-one of formula I.

The reaction of 1,6-dihydro-2-methyl-6-oxo-3-pyridinecarbonitrile with bis(di-lower-alkylamino)-t-butoxymethane of formula V $(R_2R_2N)_2CHOC(CH_3)_3$     V produces 1,6-dihydro-2-[2-(di-lower-alkylamino)-ethenyl]-6-oxo-3-pyridinecarbonitrile of formula III.

The reaction of 5-bromo(or chloro)-7-R'-1,6-naphthyridin-2(1H)-one (formula II where X is Br or Cl and R' is hydrogen or methyl) with hydrazine hydrate produces the corresponding 5-hydrazino-7-R'-1,6-naphthyridin-2(1H)-one (formula II where X is hydrazino and R' is hydrogen or methyl).

The reaction of 5-hydrazino-7-R'-1,6-naphthyridin-2(1H)-one (formula II where X is hydrazino and R' is hydrogen or methyl) with 1,1,3,3-tetramethoxypropane produces 5-(1H-pyrazol-1-yl)-7-R'-1,6-naphthyridin-2(1H)-one of formula I where Y is N, Z is C—H, R' is hydrogen or methyl and $R_1$ and R are each hydrogen.

Preferred compounds having formula I are those where Y is CH when Z is N, $R_1$ and R are each hydrogen or methyl and R' is hydrogen, or Y is N when Z is CH, R' is hydrogen and, $R_1$ and R are each hydrogen, or Y and Z are each N when R', R₁ and R are each hydrogen.

The term "lower-alkyl" as used herein, e.g., one of the meanings for R or R₁ in formula I, as C-(lower-alkyl) for one of the meanings of Z or Y in formula I, or as the meaning of R₂ or R₃ in formulas III, IIIa and IV means alkyl radicals having from 1 to 4 carbon atoms which can be arranged as straight or branched chains, illustrated by methyl, ethyl, n-propyl, isopropyl, n-butyl, sec.-butyl, tert.-butyl and isobutyl.

The term "halo" as used herein, e.g., as one of the meanings for R or R₁ in formula I or in C-halo as one of the meanings for Y or Z in formula I, preferably means bromo or chloro.

The compounds of formulas I and II are useful both in the free base form and in the form of acid-addition salts, and, both forms are within the purview of the invention. The acid-addition salts are simply a more convenient form for use; and in practice, use of the salt form inherently amounts to use of the base form. The acids which can be used to prepare the acid-addition salts of the compounds of formulas I and II include preferably those which produce, when combined with the free base, pharmaceutically acceptable salts, that is, salts whose anions are relatively innocuous to the animal organism in pharmaceutical doses of the salts, so that the beneficial cardiotonic properties inherent in the free base are not vitiated by side effects ascribable to the anions. Appropriate pharmaceutically acceptable salts within the scope of the invention are those derived from mineral acids such as hydrochloric acid, hydrobromic acid, sulfuric acid, phosphoric acid and sulfamic acid; and organic acids such as lactic acid, acetic acid, citric acid, tartaric acid, methanesulfonic acid, ethanesulfonic acid, benzenesulfonic acid, p-toluenesulfonic acid, cyclohexylsulfamic acid, quinic acid, and the like, giving the hydrochloride, hydrobromide, sulfate, phosphate, sulfamate, lactate, acetate, citrate, tartrate, methanesulfonate, ethanesulfonate, benzenesulfonate, p-toluenesulfonate, cyclohexylsulfamate and quinate, respectively.

The acid-addition salts of said basic compounds of formulas I and II are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Although pharmaceutically acceptable salts of said basic compounds of formulas I and II are preferred, all acid-addition salts are within the scope of the invention. All acid-addition salts are useful as sources of the free base form even if the particular salt per se is desired only as an intermediate product as for example when the salt is formed only for purposes of purification or identification, or when it is used as an intermediate in preparing a pharmaceutically acceptable salt by ion exchange procedures.

Other pharmaceutically acceptable salts of said compound of formulas I and II are those cationic salts derived from strong inorganic or organic bases, e.g., sodium hydroxide, potassium hydroxide, monobasic or dibasic lower-alkylamines, tetra-(lower-alkyl)ammonium hydroxides.

The molecular structures of the compounds of formulas I, II, III, IIIa and IV were assigned on the basis of evidence provided by infrared, ultraviolet, nuclear magnetic resonance and mass spectra, by the correspondence of calculated and found values for the elemental analyses, and by their method of preparation.

The manner of making and using the instant invention will now be generally descibed so as to enable a person skilled in the art of pharmaceutical chemistry to make and use the same.

The reaction of 1,6-dihydro-2-methyl-6-oxo-3-pyridinecarbonitrile with bis(di-lower-alkylamino)-t-butoxymethane to produce 2-[2-(di-lower-alkylamino)ethenyl]-1,6-dihydro-6-oxo-3-pyridinecarbonitrile of formula III is carried out by heating the reactants at about 100° C. to 160° C., preferably in a suitable aprotic solvent. The reaction is conveniently run by refluxing the reactants in dimethylformamide or dioxane (p-dioxane), preferably using bis(dimethylamino)-t-butoxymethane.

The intermediate bis(di-lower-alkylamino)-t-butoxymethanes of formula V are known compounds or are prepared by conventional means.

Alternatively, the compounds of formula III where the lower-alkyl groups R₂ and R₃ have from 2 to 4 carbon atoms are conveniently prepared by refluxing the compound of formula III where R₂ and R₃ are each methyl with an excess of the appropriate amine of the formula R₂R₃NH in methanol.

The preparation of said intermediate 1,6-dihydro-2-methyl-6-oxo-3-pyridinecarbonitrile is shown in CibaGeigy AG German Patent Publication No. 2,256,288, published May 24, 1973. 3-Aminocrotononitrile is reacted with 3-ethoxyacrylic acid chloride at −15° C. to −10° C. in a mixture of pyridine, tetrahydrofuran and dimethylformamide, and then the reaction mixture is treated with water. As shown hereinbelow, 1,6-dihydro-2-methyl-6-oxo-3-pyridinecarbonitrile was conveniently prepared by refluxing a mixture of 3-aminocrotononitrile and methyl propiolate in dimethylformamide.

The reaction of 6-methoxy-2-methyl-3-pyridinecarbonitrile with di-(lower-alkyl)acetamide dimethyl acetal to produce 2-[2-(di-lower-alkylamino)-1-propenyl)]-6-methoxy-3-pyridinecarbonitrile of formula IIIa is carried out by heating the reactants in a suitable aprotic solvent, preferably dimethylformamide, at about 120°–140° C., preferably using dimethylacetamide dimethyl acetal.

The reaction of hydrogen bromide or hydrogen chloride with 2-[2-(di-lower-alkylamino)ethenyl]-1,6-dihydro-6-oxo-3-pyridine-carbonitrile of formula III to produce 5-bromo(or chloro)-1,6-naphthyridin-2(1H)-one of formula II where X is bromo or chloro and R' is hydrogen is carried out by bubbling gaseous hydrogen bromide or hydrogen chloride into a chilled and stirred solution containing III in a suitable solvent, e.g., a mixture of chloroform and acetic acid, and then stirring the reaction mixture at room temperature.

The reaction of hydrogen bromide or hydrogen chloride with 2-[2-(di-lower-alkylamino)-1-propenyl]-6-methoxy-3-pyridinecarbonitrile of formula IIIa to produce 5-(bromo or chloro)-2-methoxy-7-methyl-1,6-naphthyridine is carried out as in the immediately preceding paragraph and then said 2-methoxy compound is treated with aqueous sodium or potassium hydroxide solution at room temperature to produce 5-(bromo or chloro)-7-methyl-1,6-naphthyridin-2(1H)-one of formula II where X is bromo or chloro and R' is methyl.

The reaction of 5-bromo(or chloro)-7-R'-1,6-naphthyridin-2(1H)-one with a 1H-(5-membered-N-aromatic)heteryl compound of formula IV to produce the 5-[1H-(5-membered-N-aromatic-heteryl)-1-yl]-7-R'-

1,6-naphthyridin-2(1H)-one of formula I is carried out by heating the reactants at about 125° C. to 225° C., preferably about 140° C. to 180° C. in a suitable inert solvent in the presence or absence of an acid-acceptor. Illustrative solvents are dimethylformamide, N-methylpyrrolidinone, and illustrative acid-acceptors are anhydrous potassium carbonate, sodium methoxide, sodium hydride, and the like. The reaction is preferably run using N-methylpyrrolidin-one as solvent and using a two-to-four fold excess, preferably three fold excess, of 1H-(5-membered-N-aromatic)-heteryl compound of formula IV per mole of 5-bromo-7-R'-1,6-naphthyridin-2(1H)-one in the absence of an acid-acceptor.

The intermediate 1H-(5-membered-N-aromatic)-heteryl compounds of formula IV are known compounds which are prepared by conventional means or are commercially available.

The reaction of 5-hydrazino-7-R'-1,6-naphthyridin-2(1H)-one with 1,1,3,3-tetramethoxypropane to produce 5-(1H)-pyrazol-1-yl)-7-R'-1,6-naphthyridin-2(1H)-one is carried out by heating the reactants in a suitable solvent, e.g., ethylene glycol, at about 150° C. to 200° C., preferably about 160° C. to 180° C.

5-Hydrazino-7-R'-1,6-naphthyridin-2(1H)-one is conveniently formed by heating 5-bromo(or chloro)-7-R'-1,6-naphthyridin-2(1H)-one with hydrazine hydrate.

The following examples will further illustrate the invention without, however, limiting it thereto.

1. 2-[2-(Dimethylamino)ethenyl]-1,6-dihydro-6-oxo-3-pyridinecarbonitrile—To a stirred mixture containing 6.7 g of 1,6-dihydro-2-methyl-6-oxo-3-pyridinecarbonitrile in 100 ml of dimethylformamide was quickly added 11.5 ml of bis(dimethylamino)-t-butoxymethane and the reaction mixture was heated with stirring for 3 hours at 110° C. After a tlc analysis had shown some of the starting material still present, another 2.3 ml of bis-(dimethylamino)-t-butoxymethane was added, the reaction mixture was heated with stirring to reflux for 90 minutes, and then allowed to cool to room temperature and stand overnight. The mixture was chilled and the separated product was collected, washed with chilled ethanol and dried in a vacuum oven at 90° C. to yield 8.2 g of 2-[2-(dimethylamino)ethenyl]-1,6-dihydro-6-oxo-3-pyridinecarbonitrile, m.p. 298°–300° C.

The above intermediate 1,6-dihydro-2-methyl-6-oxo-3-pyridinecarbonitrile was prepared as follows: a mixture containing 85% 3-amino-2-butenenitrile and 8.4 g of methyl propiolate was heated on a steam bath for about 15 minutes whereupon a vigorous exothermic reaction ensued. External heating was stopped until the reaction subsided. To the reaction mixture was added 25 ml of dimethylformamide and the reaction mixture was refluxed for 8 hours, allowed to cool to room temperature and then stand overnight. The separated solid was collected, washed with ethanol and dried in a vacuum oven at 90° C. to yield 3.4 g of 1,6-dihydro-2-methyl-6-oxo-3-pyridinecarbonitrile, m.p. >300° C.

Acid-addition salts of 2-[2-(dimethylamino)ethenyl]-1,6-dihydro-6-oxo-3-pyridinecarbonitrile are conveniently prepared by adding to a mixture of 2 g of 2-[2-(dimethylamino)ethenyl]-1,6-dihydro-6-oxo-3-pyridinecarbonitrile in about 40 ml of methanol or ethanol the appropriate acid, e.g., methanesulfonic acid, concentrated sulfuric acid, concentrated phosphoric acid, to a pH of about 2 to 3, chilling the mixture after partial evaporation and collecting the precipitate, e.g., dimethanesulfonate, sulfate, phosphate, respectively.

2. 2-[2-(Diethylamino)ethenyl]-1,6-dihydro-6-oxo-3-pyridinecarbonitrile, m.p. 218°–220° C., was prepared by refluxing 2-[2-(dimethylamino)ethenyl]-1,6-dihydro-6-oxo-3-pyridinecarbonitrile with a 3 to 4 molar excess of diethylamine for about 70 hours; the reaction mixture was allowed to cool; and, the precipitated product was collected, recrystallized from isopropyl alcohol and dried in a vacuum oven at 90° C.

Also, 2-[2-(diethylamino)ethenyl]-1,6-dihydro-6-oxo-3-pyridinecarbonitrile can be prepared following the procedure described in Example 1 using a molar equivalent quantity of bis(diethylamino)-t-butoxymethane in place of bis(dimethylamino)-t-butoxymethane.

3. 2-[2-(Di-n-propylamino)ethenyl]-1,6-dihydro-6-oxo-3-pyridinecarbonitrile, m.p. 154°–155° C., was prepared as in Example 2 but using an excess of di-n-propylamine in place of diethylamine.

4. 5-Bromo-1,6-naphthyridin-2(1H)-one—Hydrogen bromide was bubbled for about 25 minutes into a stirred suspension containing 9.5 g of 2-[2-(dimethylamino)ethenyl]-1,6-dihydro-6-oxo-3-pyridinecarbonitrile in 400 ml of chloroform cooled in an ice bath. The reaction mixture was stirred in the ice bath for 1 hour, allowed to warm up to room temperature and stirred at room temperature overnight. A tlc analysis using 7:2:1 of diethyl ether:methanol:triethylamine showed only starting material and no final product. To the reaction mixture was added 150 ml of acetic acid and hydrogen bromide was bubbled into the reaction mixture at room temperature with stirring whereupon the reaction mixture turned a lighter yellow color. The reaction mixture was then stirred at room temperature overnight and then concentrated on a rotary evaporator to dryness. The residue was stirred in an ice bath with about 300 ml of 10% aqueous potassium carbonate. The solid was collected by filtering the mixture through a sintered glass funnel, washed with water and dried in a vacuum oven at 50° C. to yield 10.5 g of 5-bromo-1,6-naphthyridin-2(1H)-one, m.p. 278°–280° C.

In subsequent runs the reaction was run starting with a mixture of chloroform and acetic acid, illustrated as follows: Into a mixture containing 40 g of 2-[2-(dimethylamino)ethenyl]-1,6-dihydro-6-oxo-3-pyridinecarbonitrile, 400 ml of chloroform and 202 ml of acetic acid, the mixture chilled in an ice bath, was bubbled hydrogen bromide for 45 minutes whereupon the reaction mixture changed from dark yellow to off white. The reaction mixture was stirred in the ice bath for 15 minutes, allowed to warm up to room temperature and then stirred at room temperature over the weekend. The precipitate was collected, washed with chloroform and dried in vacuum oven at 60° C. to yield 83 g of solid which contained some inorganic material. The solid was slurried in water along with the concentrate obtained by evaporating the mother liquor on a rotary evaporator and the mixture was stirred at room temperature. The solid was collected, washed with water and dried in a vacuum oven at 90° C. to yield 41.2 g of 5-bromo-1,6-naphthyridin-2(1H)-one, m.p. 272°–274° C.

Acid-addition salts of 5-bromo-1,6-naphthyridin-2(1H)-one are conveniently prepared by adding to a mixture of 2 g of 5-bromo-1,6-naphthyridin-2(1H)-one in about 40 ml of aqueous methanol the appropriate acid, e.g., methanesulfonic acid, concentrated sulfuric acid, concentrated phosphoric acid, to a pH of about 2–3, chilling the mixture after partial evaporation and collecting the precipitate, e.g., dimethanesulfonate, sulfate, phosphate respectively. Also, the acid-addition salt is conveniently prepared in aqueous solution by adding to water with stirring molar equivalent quantities of 5-bromo-1,6-naphthyridin-2(1H)-one and the appropriate acid, e.g., lactic acid or hydrochloric acid, to prepare respectively the monolactate or monohydrochloride salt in aqueous solution.

Cationic salts of 5-bromo-1,6-naphthyridin-2(1H)-one are conveniently prepared by reaction with an equivalent quantity of the appropriate base, e.g., sodium hydroxide, potassium hydroxide or tetramethylammonium hydroxide, to produce the corresponding respective sodium, potassium or tetramethylammonium salt. The salts are prepared in solution or in solid form by suspending equivalent quantities of 5-bromo-1,6-naphthyridin-2(1H)-one and base in water or water-methanol to form the solution of salt or by evaporating the solvent from the solution to obtain the salt in solid form.

5. 5-Chloro-1,6-naphthyridin-2(1H)-one—Following the procedure described in Example 4 using a molar equivalent quantity of hydrogen chloride in place of hydrogen bromide, it is contemplated that 5-chloro-1,6-naphthyridin-2(1H)-one can be obtained.

6. 5-(1H-imidazol-1-yl)-1,6-naphthyridin-2(1H)one—Io a solution containing 15 g of imidazole dissolved in 200 ml of dimethylformamide was added with stirring 2.7 g of sodium hydride and the resulting mixture stirred at room temperature for 10 minutes. To the reaction mixture was then added 11.3 g of 5-bromo-1,6-naphthyridin-2(1H)-one and the reaction mixture was refluxed overnight. The reaction mixture was concentrated on a rotary evaporator to remove most of the solvent. To the concentrate was added water plus 7.5 ml of concentrated hydrochloric acid and the mixture allowed to stand at room temperature. The solid that separated was collected, washed successively with water and n-hexane, and dried in a vacuum oven at 90° C. to yield 4.5 g of off-white powder. The powder was recrystallized from hot methanol, washed with methanol and dried in a vacuum oven at 90° C. to yield 4.0 g of 5-(1H-imidazol-1-yl)-1,6-naphthyridin-2(1H)-one, m.p. 291°-292° C.

Acid-addition salts of 5-(1H-imidazol-1-yl)-1,6-naphthyridin-2(1H)-one are conveniently prepared by adding to a mixture of 2 g of 5-(1H-imidazol-1-yl)-1,6-naphthyridin-2(1H)-one in about 40 ml of aqueous methanol the appropriate acid, e.g., methanesulfonic acid, concentrated sulfuric acid, concentrated phosphoric acid, to a pH of about 2 to 3, chilling the mixture after partial evaporation and collecting the precipitate, e.g., dimethanesulfonate, sulfate, phosphate, respectively. Also, the acid-addition salt is conveniently prepared in aqueous solution by adding to water with stirring molar equivalent quantities of 5-(1H-imidazol-1-yl)-1,6-naphthyridin-2(1H)-one and the appropriate acid, e.g., lactic acid or hydrochloric acid, to prepare respectively the monolactate or monohydrochloride salt in aqueous solution.

Cationic salts of 5-(1H-imidazol-1-yl)-1,6-naphthyridin-2(1H)-one are conveniently prepared by reaction with an equivalent quantity of the appropriate base, for example, sodium hydroxide, potassium hydroxide, ethylamine, trimethylamine or tetramethylammonium hydroxide, to form the corresponding respective sodium, potassium, ethylammonium, trimethylammonium or tetramethylammonium salt. The salts are prepared in solution or in solid form by suspending a equivalent quantities of said 5-(1H-imidazol-1-yl)-1,6-naphthyridin-2(1H)-one and base in water or water-methanol to form the solution of salt or by evaporating the solvent from the solution to obtain the salt in solid form.

7. 5-(4-Methyl-1H-imidazol-1-yl)-1,6-naphthyridin-2(1H)-one—A mixture containing 6.75 g of 5-bromo-1,6-naphthyridin-2(1H)-one, 7.0 g of 4-methyl-1H-imidazole and 100 ml of dimethylformamide was refluxed with stirring for 33 hours and then concentrated on a rotary evaporator. The residue was slurried in water, the mixture treated with a small quantity of acetic acid. The solid was collected, washed with water and dried in a vacuum oven at 90° C. The solid was dissolved in boiling isopropyl alcohol, the hot solution treated with decolorizing charcoal and filtered. The hot filtrate was concentrated and cooled. The separated solid was collected, washed successively with isopropyl alcohol and ether and dried in a vacuum oven at 90° C. to yield 1.9 g of product which was recrystallized a second time from isopropyl alcohol and dried under reduced pressure at 105° C. to yield 1.1 g of 5-(4-methyl-1H-imidazol-1-yl)-1,6-naphthyridin-2(1H)-one as a compound with 2-propanol (4:1) and water (4:1), m.p. 257°-259° C.

A 19.6 g portion of 5-(4-methyl-1H-imidazol-1-yl)-1,6-naphthyridin-2(1H)-one as a compound with one-fourth mole each of isopropyl alcohol and water per mole of said compound was recrystallized from 1.3 liters of ethanol and the recrystallized solid was dried at 115° C. in a drying pistol (Abderhalden) at <1 mm pressure for two days. The resulting compound, weighing 15.1 g, contained one-fourth mole of ethanol per mol of said compound. This 15.1 g portion was recrystallized from about 2500 ml of water and dried at 125° C. in a drying pistol at <1 mm pressure for three days to produce 12.0 g of 5-(4-methyl-1H-imidazol-1-yl)-1,6-naphthyridin-2(1H)-one, m.p. 263°-264° C.

Acid-addition salts and cationic salts of 5-(4-methyl-1H-imidazol-1-yl)-1,6-naphthyridin-2(1H)-one are prepared as in Example 6 following the procedures described therein.

8. 5-(2-Methyl-1H-imidazol-1-yl)-1,6-naphthyridin-2(1H)-one—A mixture containing 5.6 g of 5-bromo-1,6-naphthyridin-2(1H)-one, 8 g of 2-methyl-1H-imidazole, 25 ml of N-methylpyrrolidinone, 3.4 g of anhydrous potassium carbonate and 50 mg of copper powder was refluxed for 6 hours, allowed to cool to room temperature and then poured into 100 ml of water. The resulting solution was neutralized by adding acetic acid and the resulting solution was allowed to stand overnight at room temperature. The solid that separated was collected, recrystallized from dimethylformamide and dried in a vacuum oven at 90°-95° C. to yield 2.4 g of 5-(2-methyl-1H-imidazol-1-yl)-1,6-naphthyridin-2(1H)-one, m.p. >310° C.

9. 5-(2-Methyl-5-nitro-1H-imidazol-1-yl)-1,6-naphthyridin-2(1H)-one—A mixture containing 5.6 g of 5-bromo-1,6-naphthyridin-2(1H)-one, 12.7 g of 2-methyl-5-nitro-1H-imidazole, 3.45 g of anhydrous potassium carbonate and 50 ml of N-methylpyrrolidinone was refluxed for 5.5 hours, cooled and concentrated in vacuo to remove most of the solvent. To the concentrate was added 100 ml of water and 10 ml of 35% aqueous sodium hydroxide; and, the mixture was treated with decolorizing charcoal and filtered. The filtrate was acidified with acetic acid and the precipitate was collected, washed with water, dried, recrystallized from dimethylformamide, and dried in a vacuum oven at 90°-95° C. to yield 4.5 g of 5-(2-methyl-5-nitro-1H- imidazol-1-yl)-1,6-naphthyridin-2(1H)-one, m.p. >300° C.

10. 5-(1H-pyrazol-1-yl)-1,6-naphthyridin-2(1H)-one—To a mixture containing 5-hydrazino-1,6-naphthyridin-2(1H)-one monohydrochloride monohydrate suspended in 100 ml of methanol was added 1.35 g of sodium methoxide and the mixture stirred at room temperature for 20 minutes and then stripped to dryness in vacuo to produce 5-hydrazino-1,6-naphthyridin-2(1H)-one in free base form. To the residue was added 6.15 g of 1,1,3,3-tetramethoxypropane and 25 ml of ethylene glycol; and, the resulting mixture was heated with stirring to about 170° C., allowing the methanol boil off from the reaction mixture. The reaction mixture was allowed to stand at room temperature over the weekend and was then concentrated on a rotary evaporator. The residue was slurried in boiling methanol; and, the mixture was cooled and filtered. The solid was slurried in water, collected and dried in a vacuum oven at about 90° C. The solid was dissolved in boiling dimethylformamide, the hot solution treated with decolorizing charcoal and filtered, and, the filtrate allowed to cool. The separated product was collected, washed with methanol and dried in a vacuum oven at 90° C. to yield 2.8 g of 5-(1H-pyrazol-1-yl)-1,6-naphthyridin-2(1H)-one, m.p. >300° C.

Acid-addition salts of 5-(1H-pyrazol-1-yl)-1,6-naphthyridin-2(1H)-one are conveniently prepared by adding to a mixture of 2 g of 5-(1H-pyrazol-1-yl)-1,6-naphthyridin-2(1H)-one in about 40 ml of aqueous methanol the appropriate acid, e.g., methanesulfonic acid, concentrated sulfuric acid, concentrated phosphoric acid, to a pH of about 2 to 3, chilling the mixture after partial evaporation and collecting the precipitate, e.g., dimethanesulfonate, sulfate, phosphate, respectively. Also, the acid-addition salt is conveniently prepared in aqueous solution by adding to water with stirring molar equivalent quantities of 5-(1H-pyrazol-1-yl)-1,6-naphthyridin-2(1H)-one and the appropriate acid, e.g., lactic acid or hydrochloric acid, to prepare respectively the monolactate or monohydrochloride salt in aqueous solution.

Cationic salts of 5-(1H-pyrazol-1-yl)-1,6-naphthyridin-2(1H)-one are conveniently prepared by reaction with an equivalent quantity of the appropriate base, for example, sodium hydroxide, potassium hydroxide or tetramethylammonium hydroxide, to form the corresponding respective sodium, potassium or tetramethylammonium salt. The salts are prepared in solution or in solid form by suspending a equivalent quantities of said 5-(1H-pyrazol-1-yl)-1,6-naphthyridin-2(1H)-one and base in water or water-methanol to form the solution of salt or by evaporating the solvent from the solution to obtain the salt in solid form.

The above intermediate 5-hydrazino-1,6-naphthyridin-2(1H)-one as its monohydrochloride monohydrate was prepared as follows. A mixture containing 30 g of 5-bromo-1,6-naphthyridin-2(1H)-one and 20.2 ml of hydrazine hydrate was heated to reflux and then heated for an additional 2 hours. The reaction mixture was concentrated on a rotary evaporator and the residue was slurried in concentrated hydrochloric acid. The solid was collected, washed with concentrated hydrochloric acid, dried in a vacuum oven at 75° C. The solid was then slurried in water, collected by filtration, washed with water and dried in a vacuum oven at 90° C. to yield 25.2 g of 5-hydrazino-1,6-naphthyridin-2(1H)-one monohydrochloride monohydrate, m.p. >310° C. with decomposition.

11. 5-(1H-1,2,4-triazol-1-yl)-1,6-naphthyridin2(1H)-one—A mixture containing 5.6 g of 5-bromo-1,6-naphthyridin-2(1H)-one, 100 ml of dimethylformamide and 6.9 g of 1,2,4-triazole was refluxed on an oil bath for 21 hours and then allowed to cool. The separated solid was collected, washed with ethanol and dried in a vacuum oven at 90° C. to yield 2.8 g of 5-(1H-1,2,4-triazol-1-yl)-1,6-naphthyridin-2(1H)-one, m.p. >300° C.

Acid-addition salts of 5-(1H-1,2,4-triazol-1-yl)-1,6-naphthyridin-2(1H)-one are conveniently prepared by adding to a mixture of 2 g of 5-(1H-1,2,4-triazol-1-yl)-1,6-naphthyridin-2(1H)-one in about 40 ml of aqueous methanol the appropriate acid, e.g., methanesulfonic acid, concentrated sulfuric acid, concentrated phosphoric acid, to a pH of about 2 to 3, chilling the mixture after partial evaporation and collecting the precipitate, e.g., dimethanesulfonate, sulfate, phosphate, respectively. Also, the acid-addition salt is conveniently prepared in aqueous solution by adding to water with stirring molar equivalent quantities of 5-(1H-1,2,4-triazol-1-yl)-1,6-naphthyridin-2(1H)-one and the appropriate acid, e.g., lactic acid or hydrochloric acid, to prepare respectively the monolactate or monohydrochloride salt in aqueous solution.

Cationic salts of 5-(1H-1,2,4-triazol-1-yl)-1,6-naphthyridin-2(1H)-one are conveniently prepared by reaction with an equivalent quantity of the appropriate base, for example, sodium hydroxide, potassium hydroxide or tetramethylammonium hydroxide, to form the corresponding respective sodium, potassium or tetramethylammonium salt. The salts are prepared in solution or in solid form by suspending a equivalent quantities of said 5-(1H-1,2,4-triazol-1-yl)-1,6-naphthyridin-2(1H)-one and base in water or water-methanol to form the solution of salt or by evaporating the solvent from the solution to obtain the salt in solid form.

12. 5-(4,5-Dimethyl-1H-imidazol-1-yl)-1,6-naphthyridin-2(1H)-one—A mixture containing 12.5 g of 5-bromo-1,6-naphthyridin-2(1H)-one, 300 ml of dimethylformamide, 13.8 g of anhydrous potassium carbonate, 10.8 g of 4,5-dimethylimidazole and 200 mg of cuprous bromide was refluxed with stirring for eight hours. About 20 ml of the solvent was distilled off using a water separator to remove any moisture from the reaction mixture. The remaining reaction mixture was concentrated on a rotary evaporator. The residue was dissolved in water, acidified with acetic acid and evaporated to dryness on a rotary evaporator. The residue was treated with 50 ml of water and the brown solid was collected, washed with water, recrystallized from ethanol in the presence of decolorizing charcoal. The resulting pale yellow solid was dried at 80°-85° C. to yield 6.4 g of 5-(4,5-dimethyl-1H-imidazol-1-yl)-1,6-naphthyridin-2(1H)-one, m.p. 256°-258° C.

13. 5-(4-Phenyl-1H-imidazol-1-yl)-1,6-naphthyridin-2(1H)-one—A mixture containing 11.3 g of 5-bromo1,6-naphthyridin-2(1H)-one, 18 g of 4-phenylimidazole and 500 ml of dimethylformamide was refluxed with stirring for ninety hours and the solvent then distilled off in vacuo. The gummy residue was slurried with a mixture of 250 ml of water and 250 ml of ether until no gum remained. The remaining solid was collected, washed successively with water and ethanol, and dried in vacuo at 85° C. to yield 10.8 g of solid. This solid was suspended in 375 ml of boiling absolute ethanol and dissolved using a small amount of hot dimethylformamide.

The solution was allowed to cool in a refrigerator overnight. The white solid was collected, washed with a small quantity of cold absolute ethanol and dried in vacuo at 90° C. to yield 5.0 g of 5-(4-phenyl-1H-imidazol-1-yl)-1,6-naphthyridin-2(1H)-one, m.p. 263°–265° C. Another 1.9 g of product, m.p. 263°–265° C., was obtained from the mother liquor.

Following the procedure described in Example 4 but using in place of imidazole a corresponding molar equivalent quantity of the appropriate substituted 1Himidazole, it is contemplated that the compounds of Examples 14–24 can be obtained.

14. 5-(2,4-Dimethyl-1H-imidazol-1-yl)-1,6-naphthyridin-2(1H)-one, using 2,4-dimethyl-1H-imidazole.

15. 5-(2,4,5-Trimethyl-1H-imidazol-1-yl)-1,6-naphthyridin-2(1H)-one, using 2,4,5-trimethyl-1H-imidazole.

16. 5-(4-Methyl-5-nitro-1H-imidazol-1-yl)-1,6-naphthyridin-2(1H)-one, using 4-methyl-5-nitro-1H-imidazole.

17. 5-(2,4-Dimethyl-5-nitro-1H-imidazol-1-yl)-1,6-naphthyridin-2(1H)-one, using 2,4-dimethyl-5-nitro1H-imidazole.

18. 5-(2-Ethyl-1H-imidazol-1-yl)-1,6-naphthyridin-2(1H)-one, using 2-ethyl-1H-imidazole.

19. 5-(2-Isopropyl-1H-imidazol-1-yl)-1,6-naphthyridin-2(1H)-one, using 2-isopropyl-1H-imidazole.

20. 5-(4-Ethyl-1H-imidazol-1-yl)-1,6-naphthyridin-(1H)-one, using 4-ethyl-1H-imidazole.

21. 5-(4,5-Diethyl-1H-imidazol-1-yl)-1,6-naphthyridin-2(1H)-one, using 4,5-diethyl-1H-imidazole.

22. 5-(2-Methyl-4,5-di-n-propyl-1H-imidazol-1-yl)-1,6-naphthyridin-2(1H)-one, using 2-methyl-4,5-di-n-propyl-1H-imidazole.

23. 5-(4-Tert-butyl-1H-imidazol-1-yl)-1,6-naphthyridin-2(1H)-one, using 4-tert-butyl-1H-imidazole.

24. 5-(4,5-Di-n-butyl-1H-imidazol-1-yl)-1,6-naphthyridin-2(1H)-one, using 4,5-di-n-butyl-1H-imidazole.

Following the procedure described in Example 4 but using a molar equivalent quantity of the corresponding substituted-1-H-pyrazole in place of imidazole, it is contemplated that the compounds of Examples 25–32 can be obtained.

25. 5-(3,4-Dimethyl-1H-pyrazol-1-yl)-1,6-naphthyridin-2(1H)-one, using 3,4-dimethyl-1H-pyrazole 26. 5-(3,5-Dimethyl-1H-pyrazol-1-yl)-1,6-naphthyridin-2(1H)-one, using 3,5-dimethyl-1H-pyrazole.

27. 5-(3-Methyl-1H-pyrazol-1-yl)-1,6-naphthyridin-2(1H)-one, using 3-methyl-1H-pyrazole 28. 5-(4-Methyl-1H-pyrazol-1-yl)-1,6-naphthyridin-2(1H)-one, using 4-methyl-1H-pyrazole.

29. 5-(3,4,5-Trimethyl-1H-pyrazol-1-yl)-1,6-naphthyridin-2(1H)-one, using 3,4,5-trimethyl-1H-pyrazole.

30. 5-(4-Ethyl-3,5-dimethyl-1H-pyrazol-1-yl)-1,6-naphthyridin-2(1H)-one, using 4-ethyl-3,5-dimethyl1H-pyrazole.

31. 5-(3-n-Propyl-1H-pyrazol-1-yl)-1,6-naphthyridin-2(1H)-one, using 3-n-propyl-1H-pyrazole.

32. 5-(3-Phenyl-1H-pyrazol-1-yl)-1,6-naphthyridin2(1H)-one, using 3-phenyl-1H-pyrazole.

Following the procedure described in Example 6 using a molar equivalent quantity of the appropriate substituted-1H-1,2,4-triazole in place of 1H-imidazole, it is contemplated that the compounds of Examples 33–39 can be obtained.

33. 5-(3,5-Dimethyl-1H-1,2,4-triazol-1-yl)-1,6-naphthyridin-2(1H)-one, using 3,5-dimethyl-1H-1,2,4-triazole.

34. 5-(5-Methyl-1H-1,2,4-triazol-1-yl)-1,6-naphthyridin-2(1H)-one, using 5-methyl-1H-1,2,4-triazole.

35. 5-(3-Methyl-1H-1,2,4-triazol-1-yl)-1,6-naphthyridin-2(1H)-one, using 3-methyl-1H-1,2,4-triazole.

36. 5-(3-Phenyl-1H-1,2,4-triazol-1-yl)-1,6-naphthyridin-2(1H)-one, using 3-phenyl-1H-1,2,4-triazole.

37. 5-(3-Ethyl-1H-1,2,4-triazol-1-yl)-1,6-naphthyridin-2(1H)-one, using 3-ethyl-1H-1,2,4-triazole.

38. 5-(3-n-Propyl-1H-1,2,4-triazol-1-yl)-1,6-naphthyridin-2(1H)-one, using 3-n-propyl-1H-1,2,4-triazole.

39. 5-(3,5-Diethyl-1H-1,2,4-triazol-1-yl)-1,6-naphthyridin-2(1H)-one, using 3,5-diethyl-1H-1,2,4-triazole 40. 5-(3-Methyl-1H-pyrazol-1-yl)-1,6-naphthyridin-2(1H)-one—A stirred mixture containing 13.5 g of 5-bromo-1,6-naphthyridin-2(1H)-one, 18 ml of 3-methyl-1Hpyrazole and 75 ml of N-methylpyrrolidinone was heated in an oil bath at 170°–180° C. for 18 hours, after which a tlc analysis indicated some remaining starting material. The temperature of the oil bath was raised to 200° C.; and, the reaction mixture was heated for an additional 5 hours and then poured into water. The solid that separated was collected, dried and combined with 1.7 g of corresponding material obtained in another run starting with 2.25 g of 5-bromo-1,6-naphthyridin-2(1H)-one. The combined solids were recrystallized from dimethylformamide and dried in an oven for three days at 100° C. to yield 6.6 g of 5-(3-methyl-1H-pyrazol-1-yl)-1,6-naphthyridin-2(1H)-one, m.p. >300° C.

41. 5-(3-Methyl-1H-1,2,4-triazole-1-yl)-1,6-naphthyridin-2(1H)-one—A stirred mixture containing 13.5 g of 5-bromo-1,6-naphthyridin-2(1H)-one, 20 g of 3-methyl-1H-1,2,4-triazole and 75 ml of N-methylpyrrolidinone was heated in an oil bath at 170°–180° C. for 18 hours and then cooled to room temperature whereupon a tan solid crystallized out. The mixture was diluted by adding 125 ml of water and the separated solid was collected, washed with water, air-dried and combined with another 1.2 g sample of the same material obtained in another run starting with 2.25 g of 5-bromo-1,6-naphthyridin-2(1H)-one. The combined solids were recrystallized from dimethylformamide and dried in an oven at 95°–100° C. for three days to yield 6.1 g of 5-(3-methyl-1H-1,2,4-triazole-1-yl)-1,6-naphthyridin-2(1H)-one, m.p. >300° C.

42. 5-[4-(Hydroxymethyl)-1H-imidazol-1-yl]-1,6-naphthyridin-2(1H)-one —A mixture containing 22.5 g of 5-bromo-1,6-naphthyridin-2(1H)-one, 31.4 g of 4-(hydroxymethyl)-1H-imidazole and 75 ml of N-methylpyrrolidinone was heated with stirring in an oil bath at 135°–150° C. for 38 hours. The reaction mixture was cooled to room temperature, diluted with water and when no precipitate separated the dark solution was filtered The filtrate was concentrated in vacuo to yield a brown viscous oil which was further concentrated on a rotary evaporator to yield a brown semi-solid. Residual N-methylpyrrolidin-one was removed by heating the semi-solid residue under reduced pressure in an oil bath heated at 120°–130° C. to yield 75.4 g of a semi-solid. To this material was added 50 ml of water and the mixture was allowed to stand at room temperature for two days whereupon some light orange product crystallized. This material was collected, washed with cold water and dried. This material was recrystallized several times from water and finally from methanol, and dried in an oven at 90°–95° C. to yield 4.5 g of 5-[4-(hydroxymethyl)-1H-imidazol-1-yl]-1,6-naphthyridin-2(1H)-one, m.p. 259°–261° C.

43. 5-(4-Bromo-1H-imidazol-1-yl)-1,6-naphthyridin-2(1H)-one—A stirred mixture containing 11.25 g of 5-bromo-1,6-naphthyridin-2(1H)-one, 16.6 g of 4-bromo-1H-imidazole and 100 ml of N-methylpyrrolidinone was heated in an oil bath at 135°–140° C. for 22 hours. The reaction mixture was cooled and diluted with 200 ml of water. The resulting precipitate was collected, washed with water, air-dried, combined with 1.5 g of 5-(4-bromo-1H-imidazol-1-yl)-1,6-naphthyridin-2(1H)-one prepared in another run starting with 1.58 g of 5-bromo-1,6-naphthyridin-2(1H)-one, recrystallized twice from dimethylformamide and dried in an Abderhalden drying pistol at 90° for 22 hours, after which the sample still contained 0.2 mol of dimethylformamide per mol of product. The material was then dissolved in 100 ml of 5% aqueous sodium hydroxide solution, the solution filtered and the filtrate solidified with acetic acid. The cottony solid that crystallized out was collected, washed with distilled water and dried in an oven at 100° C. over the weekend to produce 10.3 g of 5-(4-bromo-1H-imidazol-1-yl)-1,6-naphthyridin-2(1H)-one, m.p. 278°–280° C.

44. 5-[(4-(Trifluoromethyl)-1H-imidazol-1-yl)]-1,6-naphthyridin-2(1H)-one—A stirred mixture containing 2.25 g of 5-bromo-1,6-naphthyridin-2(1H)-one, 4.1 g of 4-(trifluoromethyl)-1H-imidazole, 4.15 g of potassium carbonate in 100 ml of dimethylformamide was refluxed for 12 hours and then allowed to cool to room temperature. The insoluble inorganic material was filtered off and the filtrate was concentrated in vacuo to yield a brown gummy residue which was dissolved in 150 ml of acetonitrile, the solution treated with decolorizing charcoal and filtered, and then the filtrate concentrated to a volume of about 75 ml. The solution was chromatographed on silica gel using ether:methanol:triethylamine mixture (7:2:1) as the eluant to yield 1.1 g of the crude product.

The above preparation was repeated but changing the heating period from 12 hours to 39 hours and following the workup as above, 800 mg of the crude product was obtained.

In a third run a mixture containing 3.5 g of 5-bromo-1,6-naphthyridin-2(1H)-one, 8.5 g of 4-(trifluoromethyl)-1H-imidazole, 8.7 g of potassium carbonate and 150 ml of dimethylformamide was refluxed with stirring for 29 hours and following a work-up procedure as described in the preceding paragraphs, 1.9 g of the crude product was obtained. The three fractions of product were combined, recrystallized three times from isopropyl alcohol and dried in an oven at 100° C. for two days to yield 1.95 g of 5-[(4-trifluoromethyl)-1H-imidazol-1-yl)]-1,6-naphthyridin-2(1H)-one, m.p. 216°–218° C.

45. 2-[2-(Dimethylamino)-1-propenyl]-6-methoxy-3-pyridinecarbonitrile—A mixture containing 47.2 g of 6-methoxy-2-methyl-3-pyridinecarbonitrile, 100 ml of dimethylacetamide dimethyl acetal and 100 ml of dimethylformamide was heated with stirring in an oil bath at 130° C. for 1 hour and 45 minutes. The temperature of the oil bath was raised to 150° C. and the methanol formed by the reaction was distilled off using a 12" distillation column (Vigreux) while continuing the heating at 150° C. for 14 hours. The reaction mixture was concentrated, 50 ml of ether was added to the concentrated solution whereupon the product crystallized out. The mixture was chilled and the crystalline solid collected. The solid was washed with cold ether, dried and recrystallized from ethyl acetate using decolorizing charcoal to yield 33.5 g of 2-[2-(dimethylamino)-1-propenyl]-6-methoxy-3-pyridinecarbonitrile, m.p. 103°–104° C.

The above intermediate 6-methoxy-2-methyl-3-pyridinecarbonitrile was prepared as follows. A 69 g portion of 6-chloro-2-methyl-3-pyridinecarbonitrile was dissolved in 700 ml of warm methanol. To the solution was added with stirring 27 g of sodium methoxide whereupon an exothermic reaction ensued. After allowing the solution to cool, an additional 5 g of sodium methoxide was added and the mixture was refluxed for 15 minutes. The precipitated sodium chloride was filtered off and to the filtrate was added about 400 ml of ether, the ether solution treated with decolorizing charcoal and filtered. The filtrate was evaporated to dryness in vacuo to yield 64 g of 6-methoxy-2-methyl-3-pyridinecarbonitrile, m.p. 80°–80.5° C.

46. 5-Bromo-7-methyl-1,6-naphthyridin-2(1H)-one—Into a solution containing 10.8 g of 2-[2-(dimethylamino)-1-propenyl]-6-methoxy-3-pyridinecarbonitrile dissolved in a mixture of 25 ml of acetic acid and 150 ml of chloroform cooled in an ice-ethanol bath was bubbled hydrogen bromide gas, keeping the reaction mixture below 20° C. A solid separated and the mixture was stirred at ambient temperature for 2 hours. The solid (5-bromo-2-methoxy-7-methyl-1,7-naphthyridine) was collected, dried, suspended in 200 ml of water and neutralized by stirring with about 20 ml of 2N aqueous potassium hydroxide solution. The separated product was collected, dried and recrystallized from dimethylformamide to yield 9.0 g of 5-bromo-7-methyl-1,6-naphthyridin-2(1H)-one, m.p. 276°–278° C.

47. 7-Methyl-5-(4-methyl-1H-imidazol-1-yl)-1,6-naphthyridin-2(1H)-one—A mixture containing 9.56 g of 5-bromo-7-methyl-1,6-naphthyridin-2(1H)-one, 8.2 g of 4-methyl-1H-imidazole and 22 ml of N-methylpyrrolidin-one was heated with stirring in an oil bath at 140° C. for 20 hours. The reaction mixture containing some separated solid was diluted with about 150 ml of water and the solid was collected, triturated with water, washed with ethanol and dried to give 6.0 g of 7-methyl-5-(4-methyl-1H-imidazol-1-yl)-1,6-naphthyridin-2(1H)-one, m.p. 307°–308° C.

48. 5-(4-Nitro-1H-imidazol-1-yl)-1,6-naphthyridin-2(1H)-one—A stirred mixture containing 13.2 g of 5-bromo-1,6-naphthyridin-2(1H)-one, 20.4 g of 4-nitro-1H-imidazole and 50 ml of N-methylpyrrolidinone was heated for eight hours in an oil bath at 170°–180° C. The reaction mixture was cooled and diluted with 200 ml of water. The solid that separated was collected, washed with water and dried. The dried solid was dissolved in 350 ml of boiling dimethylformamide, the hot solution treated with decolorizing charcoal and filtered, and the filtrate concentrated on a rotary evaporator. The residue was recrystallized from dimethylformamide, dried in an oven at 90°–95° C. over the weekend to give 20.4 g of product containing some starting 4-nitro-1H-imidazole. The mixture was treated with 400 ml of 5% aqueous potassium carbonate solution for thirty minutes and then filtered. The insoluble material was filtered off and washed with water. The washings and filtrate were combined and acidified with acetic acid. The solid that separated was collected, washed with water, air-dried and recrystallized from dimethylformamide to yield 6.8 g of 5-(4-nitro-1H-imidazol-1-yl)-1,6-naphthyridin-2(1H)-one, m.p. 298°–300° C.

Following the procedure described in Example 43 but using in place of 4-bromo-1H-imidazole a molar equivalent quantity of the corresponding appropriate substituted 1H-imidazole, it is contemplated that the following compounds of Examples 49–51 can be obtained.

49. 5-(4-Chloro-1H-imidazol-1-yl)-1,6-naphthyridin-2(1H)-one, using 4-chloro-1H-imidazole.

50. 5-(4-Chloro-5-methyl-1H-imidazol-1-yl)-1,6-naphthyridin-2(1H)-one, using 4-chloro-5-methyl-1H-imidazole.

51. 5-(2-Bromo-4,5-dimethyl-1H-imidazol-1-yl)-1,6-naphthyridin-2(1H)-one, using 2-bromo-4,5-dimethyl-1H-imidazole.

Following the procedure described in Example 40 but using in place of 3-methyl-1H-pyrazole a molar equivalent quantity of the corresponding appropriate substituted 1H-pyrazole, it is contemplated that the compounds of Examples 52–55 can be obtained.

52. 5-(4-Nitro-1H-pyrazol-1-yl)-1,6-naphthyridin-2(1H)-one, using 4-nitro-1H-pyrazole.

53. 5-(4-Chloro-1H-pyrazol-1-yl)-1,6-naphthyridin-2(1H)-one, using 4-chloro-1H-pyrazole.

54. 5-(4-Hydroxymethyl-1H-pyrazol-1-yl)-1,6-naphthyridin-2(1H)-one, using 4-hydroxymethyl-1H-pyrazole.

55. 5-(3-Trifluoromethyl-1H-pyrazol-1-yl)-1,6-naphthyridin-2(1H)-one, using 3-trifluoromethyl-1H-pyrazole.

Following the procedure described in Example 41 but using in place of 3-methyl-1H-1,2,4-triazole a molar equivalent quantity of the corresponding appropriate substituted-1H-1,2,4-triazole, it is contemplated that the compounds of Examples 56–60 can be obtained.

56. 5-(3-Bromo-1H-1,2,4-triazol-1-yl)-1,6-naphthyridin-2(1H)-one, using 3-bromo-1H-1,2,4-triazole.

57. 5-(3-Bromo-5-methyl-1H-1,2,4-triazol-1-yl)-1,6-naphthyridin-2(1H)-one, using 3-bromo-5-methyl-1H-1,2,4-triazole.

58. 5-(5-Chloro-1H-1,2,4-triazol-1-yl)-1,6-naphthyridin-2(1H)-one, using 5-chloro-1H-1,2,4-triazole.

59. 5-(3-Nitro-1H-1,2,4-triazol-1-yl)-1,6-naphthyridin-2(1H)-one, using 3-nitro-1H-1,2,4-triazole.

60. 5-(3-Trifluoromethyl-1H-1,2,4-triazol-1-yl)-1,6-naphthyridin-2(1H)-one, using 3-trifluoromethyl-1H-1,2,4-triazole.

61. Following the procedure described in Example 10 but using in place of 5-hydrazino-1,6-naphthyridin-2(1H)-one a molar equivalent quantity of 5-hydrazino-7-methyl-1,6-naphthyridin-2(1H)-one, it is contemplated that 7-methyl-5-(1H-pyrazol-1-yl)-1,6-naphthyridin-2(1H)-one can be obtained. The intermediate 5-hydrazino-7-methyl-1,6-naphthyridin-2(1H)-one can be prepared by the procedure described in Example 10 for preparing 5-hydrazino-1,6-naphthyridin-2(1H)-one but using a molar equivalent quantity of 5-bromo-7-methyl-1,6-naphthyridin-2(1H)-one in place of 5-bromo-1,6-naphthyridin-2(1H)-one.

The usefulness of the compounds of formulas I and II as cardiotonic agents is demonstrated by their effectiveness in standard pharmacological test procedures, for example, in causing a significant increase in contractile force of the isolated cat or guinea pig atria and papillary muscle and/or in causing a significant increase in cardiac contractile force in the anesthetized dog with lower or minimal changes in heart rate and blood pressure. Detailed descriptions of these test procedures appear in U.S. Pat. No. 4,072,746, issued Feb. 7, 1978.

Cardiotonic activity in said isolated cat or guinea pig atria and papillary muscle procedure, is indicated by a significant increase, that is, greater than 25% (cat) or 30% (g.pig) in papillary muscle force and a significant increase, that is, greater than 25% (cat) or 30% (g.pig) in right atrial force, with a lower percentage increase (about one-half or less than the percentage increase in right atrial force or papillary muscle force) in right atrial rate. Because of the lower control active tensions of guinea pig tissues, the percent change from control values of both rate and force responses is elevated slightly, i.e., 5%. Thus, whereas cardiotonic activity is ascertained with a papillary muscle force or right atrial force increase of 26% and greater in the cat test, corresponding activity in the guinea pig test is designated with a papillary muscle force (PMF) or right atrial force (RAF) increase of 31% or greater. Representative examples of the compounds of Formulas I and II were tested by said guinea pig atria and papillary muscle procedure with the following results:

| Example | Dose µg/ml | % Change from Control RAF | PMF |
|---|---|---|---|
| 6 | 3 | 70 | 55 |
|  | 10 | 68 | 90 |
|  | 30 | 142 | 96 |
| 7 | 0.3 | 28 | 53 |
|  | 1 | 49 | 66 |
|  | 3 | 88 | 87 |
| 8 | 10 | 39 | 34 |
|  | 30 | 117 | 69 |
|  | 100 | 221 | 100 |
| 9 | 10 | 15 | 24 |
|  | 30 | 16 | 43 |
|  | 100 | 116 | 103 |
| 10 | 10 | 38 | 43 |
|  | 30 | 102 | 121 |
|  | 100 | 168 | 203 |
| 11 | 3 | 28 | 51 |
|  | 10 | 31 | 76 |
|  | 30 | 140 | 108 |
| 12 | 3 | 7 | 13 |
|  | 10 | 14 | 49 |
|  | 30 | 50 | 92 |
| 13 | 10 | 33 | 25 |
|  | 30 | 24 | 34 |
|  | 100 | 1* | 36 |
| 47 | 1 | 37 | 46 |
|  | 3 | 46 | 48 |
|  | 10 | 158 | 164 |
| 42 | 1 | −2 | 9 |
|  | 3 | 8 | 48 |
|  | 10 | 37 | 112 |
| 44 | 10 | 35 | 30 |
|  | 30 | 36 | 31 |
|  | 100 | 101 | 69 |
| 43 | 1 | 35 | 47 |
|  | 3 | 43 | 71 |
|  | 10 | 56 | 128 |
| 41 | 1 | 29 | 36 |
|  | 3 | 37 | 56 |
|  | 10 | 67 | 124 |
| 40 | 3 | 26 | 24 |
|  | 10 | 89 | 64 |
|  | 30 | 84 | 97 |
| 4 | 3 | 57. | 73 |
|  | 10 | 49 | 85 |
|  | 30 | 134 | 110 |
| 48 | 10 | 18 | 37 |
|  | 30 | 42 | 71 |
|  | 100 | 170 | 107 |
| 46 | 1 | 41 | 44 |
|  | 3 | 92 | 67 |
|  | 10 | 59 | 114 |

*Precipitated in bath.

When tested by said anesthetized dog procedure, the said cardiotonically active compounds of formulas I and II at doses of from about 0.030 to 3.0 mg/kg administered intravenously are found to cause significant increases, that is, 25% or greater, in cardiac contractile force or cardiac contractility with lower changes in heart rate and blood pressure. Representative examples of the invention were tested by this procedure and found to cause increases in contractile force as follows:

| Example | Dose mg/kg | % Increase In Contractile Force |
|---------|------------|-------------------------------|
| 4 | 0.100 | 135 |
| 7 | 0.030 | 34 |
|   | 0.100 | 96 |
|   | 0.300 | 124 |
| 12 | 1.00 | 54 |
|    | 3.00 | 136 |
| 13 | 1.00 | 40 |
|    | 3.00 | 87 |
| 47 | 0.100 | 71 |
|    | 0.300 | 125 |
|    | 1.00 | 183 |

The present invention includes within its scope a cardiotonic composition for increasing cardiac contractility, said composition comprising a pharmaceutically acceptable carrier and, as the active component thereof, the compound of formula I or·II or pharmaceutically acceptable acid-addition or cationic salt thereof. The invention also includes within its scope the method for increasing cardiac contractility in a patient requiring such treatment which comprises administering to such patient a cardiotonically effective amount of said cardiotonically active compound of formula I or II. In clinical practice said compound will normally be administered orally or parenterally in a wide variety of dosage forms.

Solid compositions for oral administration include compressed tablets, pills, powders and granules. In such solid compositions, at least one of the active compounds is admixed with at least one inert diluent such as starch, calcium carbonate, sucrose or lactose. These compositions may also contain additional substances other than inert diluents, e.g., lubricating agents, such as magnesium stearate, talc, and the like.

Liquid compositions for oral administration include pharmaceutically acceptable emulsions, solutions, suspensions, syrups and elixirs containing inert diluents commonly used in the art, such as water and liquid paraffin. Besides inert diluents such compositions may also contain adjuvants, such as wetting and suspending agents, and sweetening, flavoring, perfuming and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. These compositions can also contain adjuvants such as stablilizing, preserving, wetting, emulsifying and dispersing agents.

They can be sterilized, for example by filtration through a bacterial-retaining filter, by incorporation of sterilizing agents in the compositions, by irradiation or by heating. They can also be manufactured in the form of sterile solid compositions which can be dissolved in sterile water or some other sterile injectable medium immediately before use.

The percentage of active component in the said composition and method for increasing cardiac contractility can be varied so that a suitable dosage is obtained. The dosage administered to a particular patient is variable, depending upon the clinician's judgement using as the criteria: the route of administration, the duration of treatment, the size and condition of the patient, the potency of the active component and the patient's response thereto. An effective dosage amount of active component can thus only be determined by the clinician considering all criteria and utilizing his best judgement on the patient's behalf.

We claim:

1. 2-[2-(di-lower-alkylamino)-1-propenyl]-6-methoxy-3-pyridinecarbonitirle having the formula IIIa

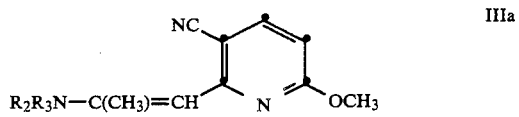

and acid-addition salt thereof, where $R_2$ and $R_3$ are each lower-alkyl.

2. 2-[2-(Dimethylamino)-1-propenyl]-6-methoxy-3-pyridinecarbonitrile, according to claim 1.

* * * * *